United States Patent
Páll et al.

(10) Patent No.: US 8,100,354 B2
(45) Date of Patent: Jan. 24, 2012

(54) APPARATUS FOR PROCESSING UTILITY WASTE WITH BIODEGRADABLE ORGANIC MATERIAL CONTENT

(75) Inventors: Ernö Páll, Budapest (HU); Ferenc Töröcsik, Szolnok (HU); Gyözö Barabás, Érd (HU); Mihály Szilágyi, Budapest (HU); István Hajdú, Besenyszög (HU)

(73) Assignee: Veolia Bioenergy Europe Kft., Budapest (HU)

( * ) Notice: Subject to any disclaimer, the term of this patent is extended or adjusted under 35 U.S.C. 154(b) by 166 days.

(21) Appl. No.: 12/532,792

(22) PCT Filed: Mar. 27, 2008

(86) PCT No.: PCT/HU2008/000030
§ 371 (c)(1),
(2), (4) Date: Nov. 5, 2009

(87) PCT Pub. No.: WO2008/117096
PCT Pub. Date: Oct. 2, 2008

(65) Prior Publication Data
US 2010/0078512 A1    Apr. 1, 2010

(30) Foreign Application Priority Data
Mar. 28, 2007   (HU) .................................. 0700246

(51) Int. Cl.
*B02C 19/22* (2006.01)

(52) U.S. Cl. ...................... 241/73; 241/260.1

(58) Field of Classification Search .................. 241/73, 241/260.1
See application file for complete search history.

(56) References Cited

U.S. PATENT DOCUMENTS

| | | | | |
|---|---|---|---|---|
| 2,571,300 | A | * | 10/1951 | Simpson .................... 241/101.8 |
| 4,511,370 | A | | 4/1985 | Hunziker et al. |
| 4,609,460 | A | | 9/1986 | Vellinga |
| 4,921,176 | A | | 5/1990 | Kunisada et al. |
| 5,431,819 | A | | 7/1995 | Hack et al. |
| 5,527,464 | A | | 6/1996 | Bartha et al. |
| 5,667,151 | A | * | 9/1997 | Miura et al. .................... 241/20 |
| 5,799,884 | A | * | 9/1998 | Alavi .............................. 241/27 |
| 7,175,115 | B1 | | 2/2007 | Gali |
| 2009/0032464 | A1 | | 2/2009 | Noguchi et al. |

FOREIGN PATENT DOCUMENTS

| | | |
|---|---|---|
| CA | 2008340 A1 | 7/1991 |
| CA | 2 376 994 A1 | 1/2001 |
| DE | 42 01 166 A1 | 7/1993 |
| DE | 196 28 521 A1 | 1/1998 |
| EP | 0 179 045 A2 | 4/1986 |
| EP | 0 679 719 A2 | 11/1995 |
| EP | 0 903 183 A1 | 3/1999 |
| EP | 0 909 586 A1 | 4/1999 |
| HU | 200139 B | 4/1990 |
| WO | 94/19119 | 9/1994 |

\* cited by examiner

*Primary Examiner* — Mark Rosenbaum
(74) *Attorney, Agent, or Firm* — Jason D. Voight

(57) ABSTRACT

An apparatus containing crushing screws (11) of the same pitch direction and without central shaft, provided with short drive shafts (112) on their driven end, wherein the rotational axis of the discharging screw (151) and the plane determined by the rotational axes of the two crushing screws (11) define an acute angle.

8 Claims, 4 Drawing Sheets

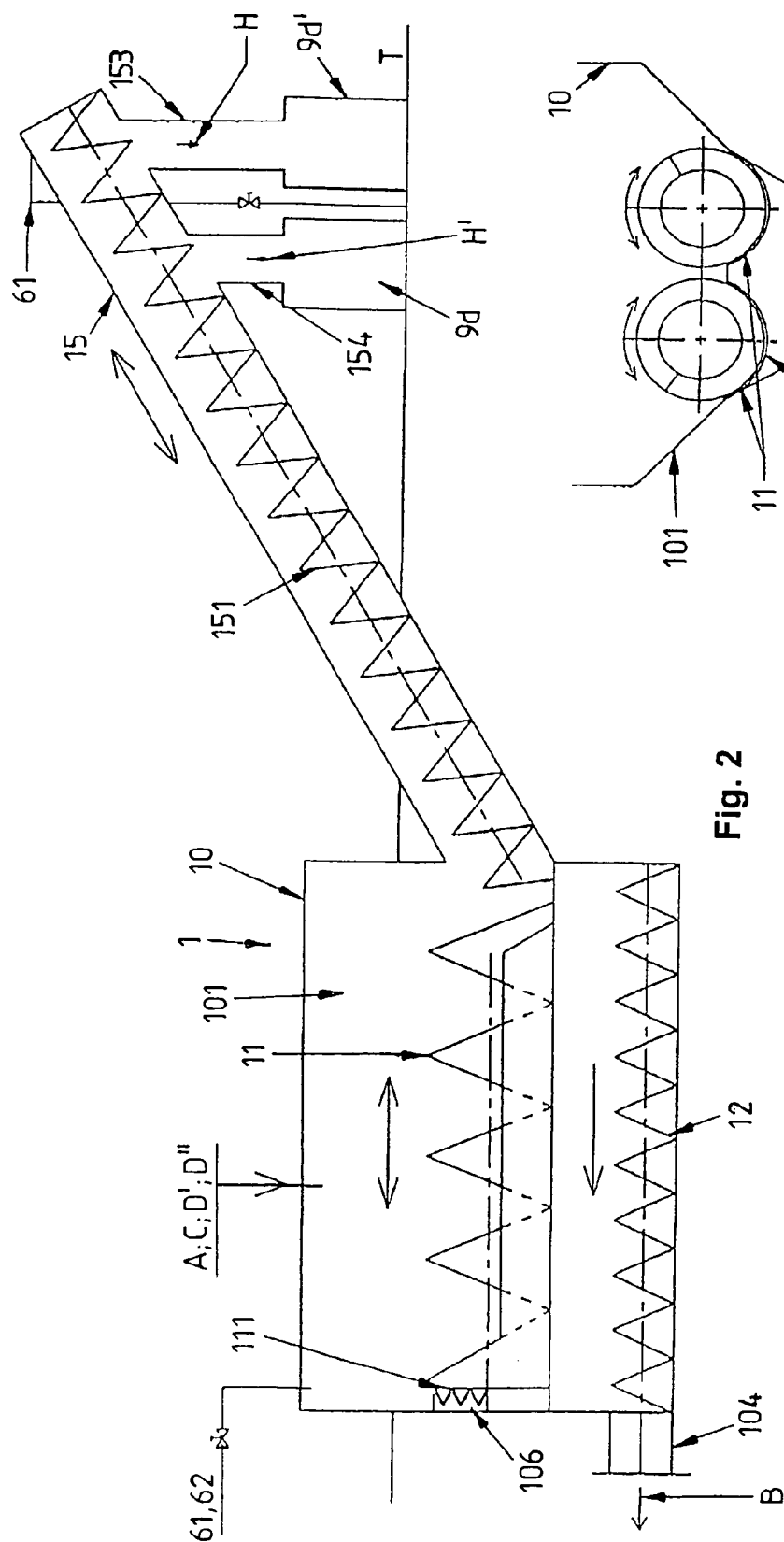

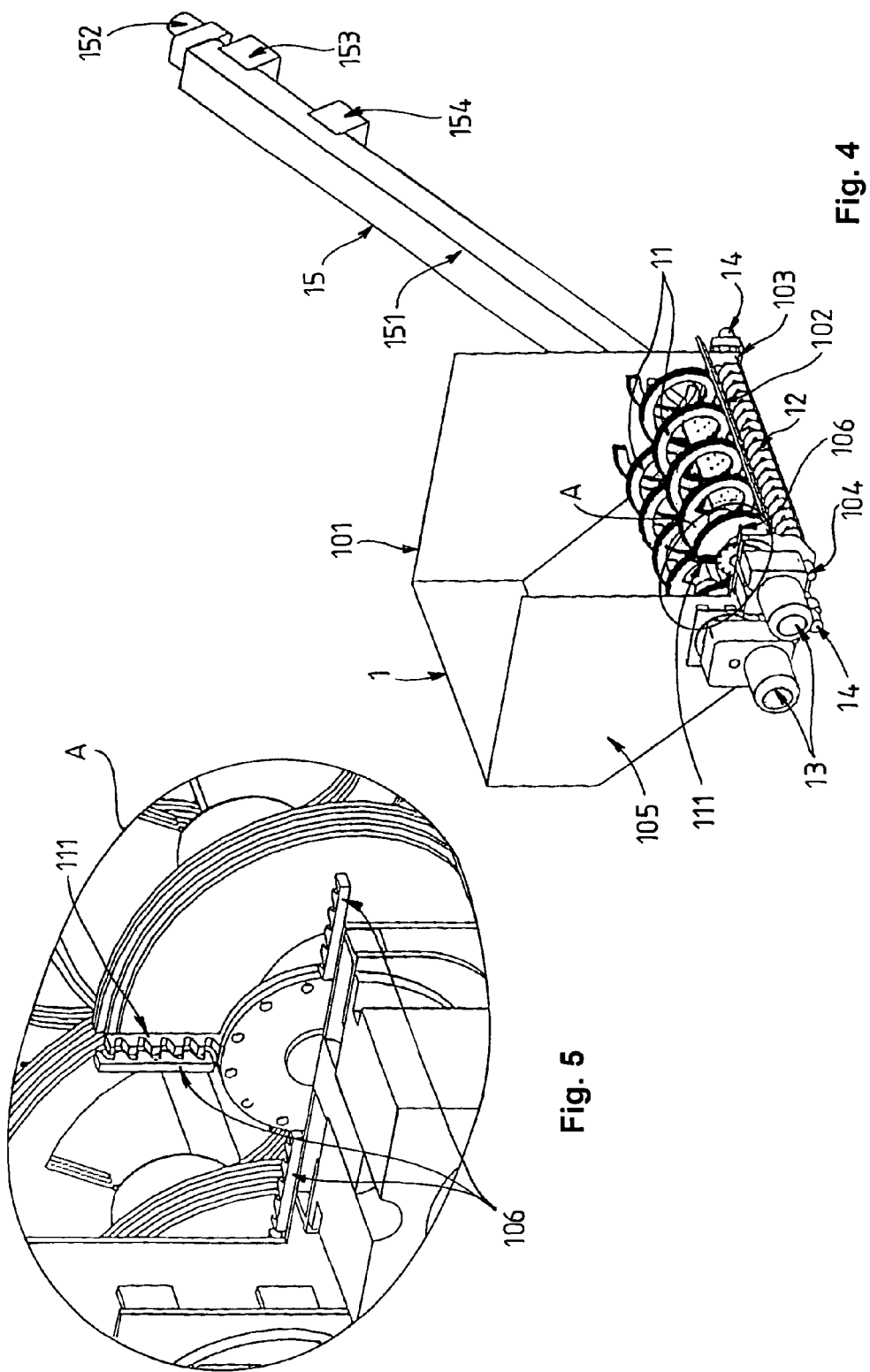

US 8,100,354 B2

APPARATUS FOR PROCESSING UTILITY WASTE WITH BIODEGRADABLE ORGANIC MATERIAL CONTENT

This is the National Stage of International Application PCT/HU2008/000030 filed Mar. 27, 2008.

The invention relates to an apparatus for processing utility waste of the type of biomass, in particular crushing and sorting unit for sewage sludge, wastes of animal protein processing, wastes of dairy industry, kitchen wastes, greasy sewage, etc. having biodegradable organic material content.

Due to the increasingly stricter regulations of environment protection, the problem of treating and degrading/eliminating wastes containing organic materials becomes more and more severe.

As a result of the sewage purification technologies, an extremely high amount of sewage sludge containing organic materials is produced in the sewage purification plants of the settlements.

The problem of treatment of sewage sludge can be regarded as solved. In the most common solution, the properly concentrated sewage sludge is fed into a mezophilic and/or thermophilic fermentation tank, in which, after an anaerobic treatment, biogas releases from the organic material component. This biogas is typically used for in-situ production of electricity.

U.S. Pat. No. 4,921,176 and EP 0 903 183 disclose apparatuses for reducing and crushing coarse material. These apparatuses comprise at least two rollers or drums in side by side substantially parallel relation. The rollers or drums are provided with cutting disks and/or ribs formed by two threads for crushing the material fed into the apparatus.

In this type of apparatuses, the movement performed by said ribs and disks crushes the material and produces a homogenous mixture of predetermined grain size, wherein the mixture contains all the fluid and hard material fed into the apparatus.

There is a need, however to treat solid material and fluids, mainly organic fluids separately, and therefor to provide an apparatus for crushing the solid part of the waste material and, at the same time, to separate the crushed solid material and the fluids.

An object of the present invention is therefore to provide means for economically and reliably processing various biodegradable organic materials, together with crushed solid material in a single system, by applying an apparatus for crushing and sorting the solid material and separating the fluid material, at the same time.

The invention is based on the idea that the very high amount of sewage sludge produced in the sewage sludge purification plants of the settlements day by day and the high amount of household garbage and municipal waste produced in the same settlements, all containing organic materials can be treated together in a complex and economic manner.

We also recognised that the solid and/or liquid wastes containing solid materials, as well as biologically non-degradable mixed empties may be crushed and separated into a biologically degradable organic fraction and a biologically non-degradable fraction in one step, in a properly designed apparatus comprising crushing screws, stirring screws, discharging screws and briar teeth.

Accordingly, the crushing and sorting apparatus according to the invention comprises receiving tray, crushing screws and driving units, wherein the bottom plate of the receiving tray is perforated and formed as a screw house with an open upper part for receiving a twin screw, two crushing screws are arranged in said screw house; a chamber is formed under the bottom plate in order to accommodate one or more stirring screws; and a discharging assembly having a discharging screw is arranged at the end of the receiving tray opposite to the crushing screw driving unit, in such a way that the free end of the discharging screw opposite to the discharging screw driving unit intrudes into the operational space of the receiving tray), wherein the crushing screws are screws of the same pitch direction and without central shaft, provided with short drive shafts on their driven end, wherein the rotational axis of the discharging screw and the plane determined by the rotational axes of the two crushing screws define an acute angle.

On the end plate of the receiving tray there are preferably a plurality of briar teeth and a plurality of bits are preferably arranged on the end of the crushing screw.

The pitches of crushing screws may be made of multilayer metal sheets, are preferably identical with each other and adapted to rotate independently of each other meanwhile their rotational speed may be adjustable. The non-driven end of the crushing screws is arranged close to the end wall.

The discharging screw may turn back-and-forth and there may be one or more separate discharge hoppers on the discharging assembly.

The heat treatment tank may be provided with internal and/or external, and the mixing tank with external heat insulation. The volume of the heat treatment tank is preferably less than the volume of the mixing tank.

The invention will now be described in more detail with reference to the accompanying drawings.

FIG. 2 shows a basic schematic line diagram of an exemplary embodiment of the crushing and sorting apparatus according to the invention, along a main sectional plane.

FIG. 3 is a schematic line diagram of the crushing and sorting apparatus shown in FIG. 2, along a transversal sectional plane.

FIG. 4 shows a schematic axonometric view of an exemplary embodiment of the crushing and sorting apparatus according to the invention, partly in section.

FIG. 5 is an enlarged detail (A) of FIG. 4

Figure 6:
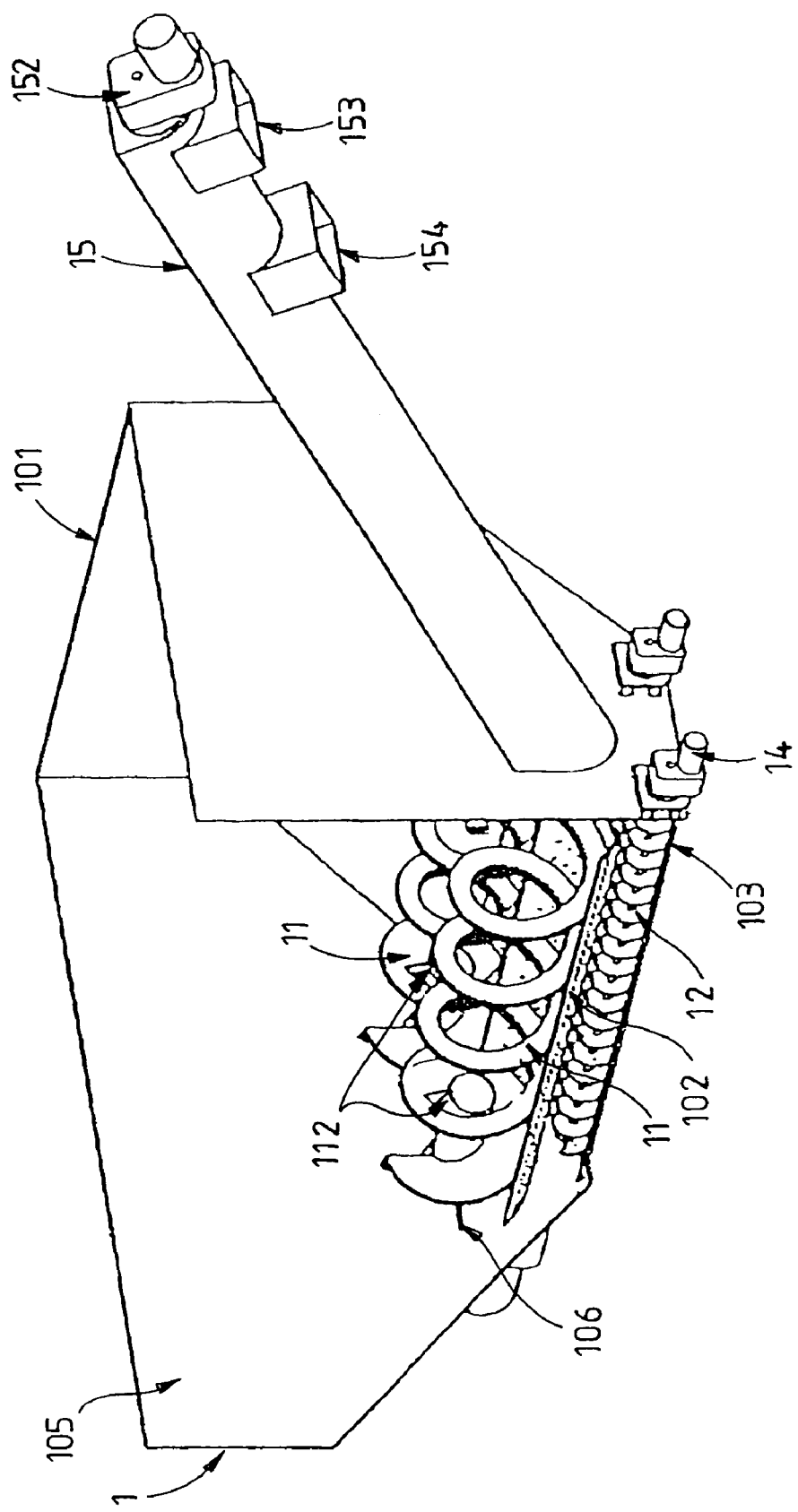

FIG. 6. shows a schematic axonometric view of the embodiment of the crushing and sorting apparatus shown in FIG. 4 as viewed from another viewing point.

For the sake of simplicity and better understanding of the description, the following references are used:

the solid wastes and/or the mixture of solid and liquid wastes are referred to as mixed waste A, independently of their content;

the liquid waste is referred to as liquid waste C, independently of its content;

the sewage sludge produced in place is referred to as sewage sludge D;

the delivered sewage sludge having a solid material content equal to or less than 6% is referred to as sewage sludge D';

the delivered sewage sludge having a solid material content more than 6%, but less than 25% is referred to as sewage sludge D".

Figure 1:
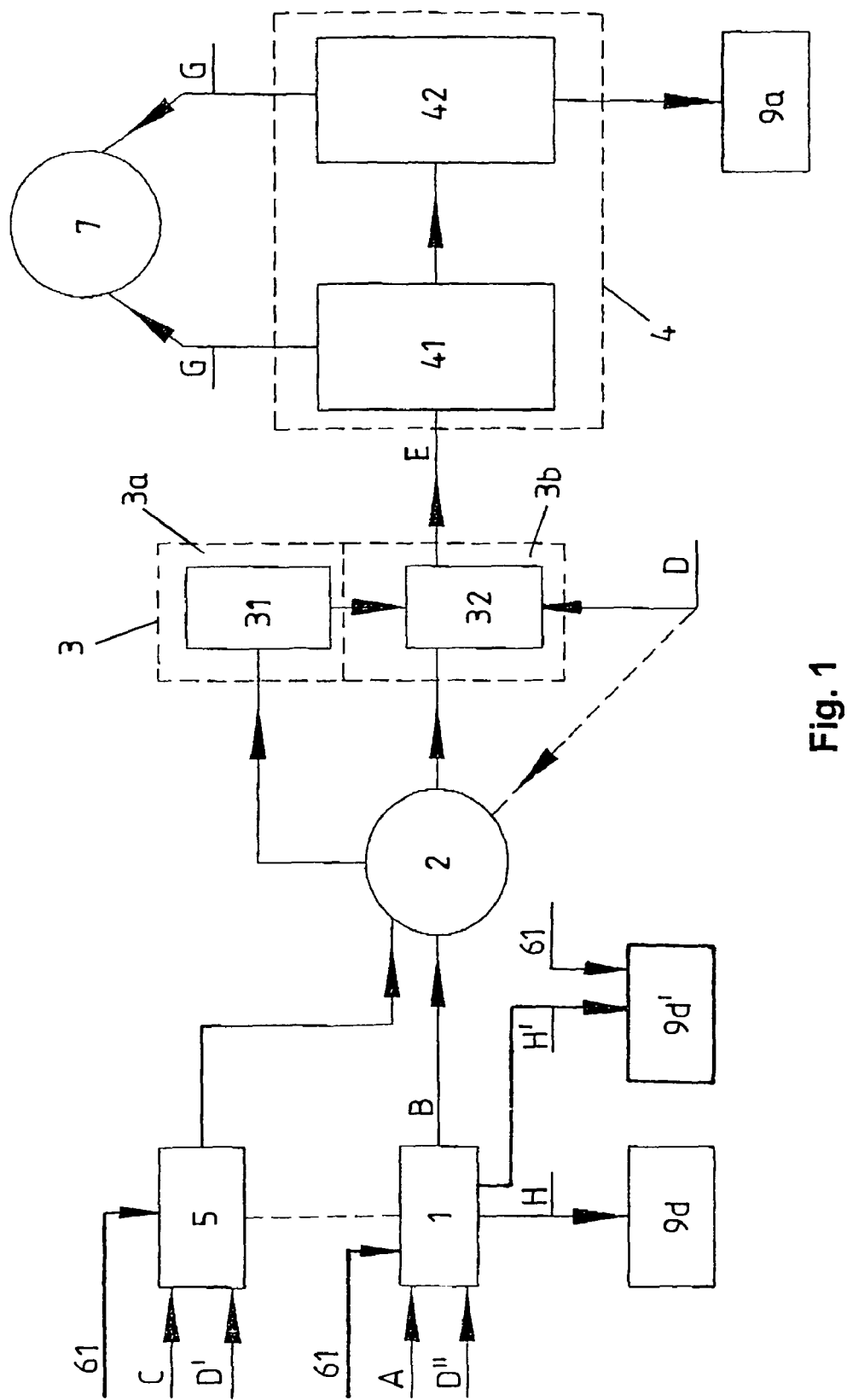
FIG. 1 illustrates the block diagram of a system applying the apparatus according to the invention.

As shown in FIG. 1 the mixed waste A and/or the sewage sludge D" are fed into the crushing and sorting apparatus 1. Alternatively, the liquid waste C and/or the sewage sludge D' may also be fed into the system at this point.

The apparatus is used for crushing the waste into chips of appropriate size—up to 8 mm—, and for separating the biologically non-degradable materials from the organic fraction.

Hereafter the biologically degradable organic fraction will be referred to as organic fraction B, whereas the biologically non-degradable fraction will be referred to as wastes H and H'.

Waste H contains mainly inorganic materials.

Waste H' is a non-usable waste that contains a small amount of organic material as well.

The organic fraction B of the mixed waste A is directed from the crushing and sorting apparatus 1 into the mixing tank 32 or into the heat treatment tank 31 of the heat treatment/mixing unit 3 corresponding to the position of the switching unit 2.

In case the waste, like the kitchen waste, requires pasteurisation because of its content, the waste is first directed into the heat treatment tank 31 and then into the mixing tank 32. When pasteurisation is not necessary, these wastes are directly fed into the mixing tank 32.

The biologically non-usable waste fractions H and H' of the mixed waste A are directed from the crushing and sorting apparatus 1 into waste collection tanks 9d and 9d', respectively, for further external processing.

The liquid waste C and/or the sewage sludge D' are directed also through the drawing-off station 5 into the mixing tank 32 or the heat treatment tank 31 of the heat treatment/mixing unit 3 corresponding to the position of the switching unit 2.

The appropriately pre-treated sewage sludge D and/or sewage sludge D' are fed into the mixing tank 32 of the heat treatment/mixing unit 3.

It is a matter of course that similarly to the organic fraction B and the liquid waste C, the sewage sludge D and/or the sewage sludge D' may also be fed through the switching unit 2 in the same way as mentioned before.

The sludge composition E is fed into the fermentation unit 4. It is preferred that the fermentation unit 4 comprises both of a thermophilic unit 41 and a mezophilic unit 42.

The fermentation unit 4 is used to ferment the sludge composition E previously fed and to produce biogas from it.

The biogas G is directed from the fermentation unit 4 into the gas tank 7 for further processing. The fermented sludge, also referred to as fermented sludge F, is convayed into the sludge treating block 9a for further processing.

FIGS. 2 to 5 show an exemplary embodiment of the crushing and sorting apparatus 1 according to the invention, which comprises a hopper 101 for receiving the mixed waste A and/or the liquid waste C and/or the sewage sludge D'' and for storing them during the processing. The crushing and sorting unit apparatus 1 further comprises a perforated filtering bottom plate 102 in the form of a screw house with an open upper part, a chamber 103 arranged under said bottom plate 102, a suction stub 104 connected the chamber 103 for discharging the organic fraction B of the processed waste, a receiving tray arranged on the end wall 105 and provided with briar teeth 106, two crushing screws 11 arranged in the filtering bottom plate 102, one or more sliding screws 12 arranged in the chamber 103, driving units 13 for the crushing screws 11, one or more driving unit 14 for each of the sliding screws 12, a discharging assembly 15 equipped with a discharging screw 151 for discharging the biologically non-degradable fraction of the chipped waste, i.e. the wastes H and H', said discharging assembly 15 being arranged at the end of the receiving tray 10 opposite to the driving units of the crushing screws and provided with a discharging screw driving unit 152.

The discharging assembly 15 has one or more discharging hoppers, in case of the above mentioned embodiment, two discharging hoppers 153, 154, for discharging the wastes H and H'.

The crushing and sorting apparatus 1 is further provided with an industrial water supplying pipe system 61 and a hot water supplying pipe system 62.

The most important feature of the receiving tray 10 is the perforated filtering bottom plate 102 formed as a screw house with an open upper part, in which two crushing screws 11 are arranged in parallel. The hopper 101 above the crushing screw 11 forms a high capacity storage volume for receiving a large amount of waste at a time.

The filtering bottom plate 102 of the receiving tray 10 formed as screw house with an open upper part is perforated and adapted to properly guide the two crushing screws separately while preventing them from being offset from their rotational axes. The curvature of the filtering bottom plate 102 is very similar to the curvature of the crest edge of the two crushing screws 11. The filtering bottom plate 102 is removable and in case of wearing, it may be replaced. The pattern of the perforation may be arbitrary, whereas the recommended maximum size of the perforations D is 10 or rather 8 mm, which allows solid materials still acceptable to pass therethrough into the fermenter. Anyway, in several cases the size of the perforations may be up to 12 mm. Beneath the filtering bottom plate 102, there is a chamber 103 for receiving the liquid, biologically degradable material, i.e. the mixed waste A and/or the liquid waste C and/or the organic fraction B of the sewage sludge D'', all of them being fed into the receiving tray 10. Inside the chamber 103, one or more sliding screws 12 rotate to prevent any deposition or blockage from being developed which would result in a malfunction. The suction stub 14 of the pump used to convey the organic fraction B for further processing is connected to the chamber 103, the outlet of said suction stub being scraped, cleaned and loosened by one of the sliding screws 12 of the chamber in order to prevent any deposition from being developed on the suction stub 104.

The two crushing screws 11 of the crushing and sorting unit apparatus 1 is used to carry out the substantial preparation and processing operations. Its operation is supported by its construction. The pitch and the rotational direction of the two crushing screws 11 are identical (both of the screws are either right-handed or left-handed), thus their mutual seizure may be avoided even if the crushing screws 11 rotate independently of each other. Due to the independent rotation of the crushing screws, the material in the receiving tray 10 may be forced to flow in various directions while being stirred and chipped. Both of the crushing screws 11 are formed without a central shaft, except a down-stream section of the driving unit, where they are provided with a short stub shaft 112. The section without shaft is required to have high elasticity and flexibility, on the one hand, and high strength and high torque transmission capability, on the other hand. Accordingly, it is made of a multilayer plate resulting in high flexibility while having high strength, heavy weight and high torque tolerating capability at the same time. It has another very important feature: it has the greatest possible diameter. The good preparation capability is due to all of its diameter, its flexibility, its weight and its torque tolerating capability.

The big solid, occasionally frozen pieces of material are chopped and disgregated by the two crushing screws 11 at a high efficiency. The filtering bottom plate 102 can clean and open up the blocked perforations easily due to its capability of easily fitting and easily evading obstacles as a result of its flexibility, despite of its weight. It tears hardly any perforation and due to its flexibility, it evades the forces in spite of that there may be obstacles. A large diameter of at least 700 mm allows solid materials (e.g. empties: cans, bottles, boxes and other containers) to enter in or exit from between the screw threads. Due to the absence of shaft, the flow is also allowed inside the closed space of the screw leaf adjacent to the rotational axis, therefore it performs a very definite and efficient crushing and recovering operation of the bulk of the organic material.

The double crushing screw 11 has a further feature. At the end adjacent to its driving unit and to its short screw section with shaft, a cutting-tearing-crumbling mechanism with a plurality of bits 111 is formed. According to the briar teeth 106 arranged on the end plate 105 of the receiving tray 10, there is provided a stationary row of bits, whereas on the end of the rotational crushing screw 11, a moving row of bits is arranged, as it is obvious from the above mentioned features. Thus the solid pieces in the material flow moving towards the wall having the stationary bits, including the beer cans as well, will be cut off and made suitable for emptying.

The discharging assembly 15 equipped with a discharging screw 151 and a discharging screw driving unit 152 for discharging the biologically non-degradable fraction of the chipped waste, i.e. the waste H, is arranged at the end of the receiving tray 10 opposite to the driving unit of the crushing screw 13. The axis of the discharging screw 151 and the plane determined by the axes of the crushing screws 11 define an acute angle. The discharging assembly 15 starts to operate only when the charged waste has been recovered, the major part of the organic fraction B has passed the perforation and substantially, only the leached empties, solid pieces and other wastes H have been retained.

The two crushing screws 11 are driven by means of a frequency converter. It is preferred that an operator can control the rotational direction and the shut-down of the crushing screws 11 independently by using a radio frequency, portable switching device, thus it becomes possible for a properly skilled operator to mix materials that contain pieces with size or condition which may be dangerous for the machine. The non-driven end of the twin screw is close to the end wall, thus the waste can be efficiently discharged without leaving a dead zone.

In a preferred embodiment the hopper 101 of the receiving tray 10 can be opened mechanically, and can be closed for safety reasons, which allows to reduce the effects of smell and noise. A suction cleaning system may also be connected thereto. For dilution and flushing, hot flush water may be introduced into the inner space of the receiving tray 10.

In order to allow an even better flush, shower-like water injection should be provided. It is recommended to return some sludge from the fermenter. Optionally, the pump conveying from the apparatus to the fermenter is adapted for recirculation so that a larger portion of the organic material can be washed.

In a preferred embodiment, the discharging assembly is a high-performance machine as the discharging assembly 15 may be filled up with material being fed into the receiving tray 10 for separation. The discharging screw 151 of the discharging assembly 15 is than to be rotated in reverse direction in order to return the mass with high organic content to the receiving tray 10 for separation. In order to better compress the waste, the screws should be able lifting the waste up to the half level, followed by returning and repressing it.

On the discharging assembly 15, two discharging hopper 153, 154 are mounted for depositing the wastes H and H' in different directions by type.

Under the discharging hoppers 153, 154, a compressing machine may be arranged that compresses the foreign packaging materials to be conveyed to the smallest possible volume. The bottom plate of the concrete object lowered beneath the ground level for receiving the apparatus is inclined and has an accumulating dibhole for collecting the escaped liquids.

For the installation of the crushing and sorting apparatus 1, it is recommended that the apparatus should be accessible by lorries and heavy trucks and the road surface T in front of the apparatus should be available for transportation manipulations. The apparatus should protrude from the plane of the road surface T at a minimum level in such a way that the plane of the hopper extends at a distance of up to 500-1000 mm from the road surface. The protrusion is provided to avoid an accident, however an excessive protrusion would make it impossible for the tip lorries to reverse and to discharge its load.

By using an adjustable protective screen, however, an adequate prevention of accidents may be reached.

The invention claimed is:

1. A crushing and sorting apparatus comprising a receiving tray, crushing screws and driving units, wherein the bottom plate (102) of the receiving tray (10) is perforated and formed as a screw house with an open upper part for receiving a twin screw, two crushing screws (11) are arranged in said screw house; a chamber (103) is formed under the bottom plate (102) in order to accommodate one or more stirring screws; and a discharging assembly (15) having a discharging screw (151) is arranged at the end of the receiving tray (10) opposite to the crushing screw driving unit, in such a way that the free end of the discharging screw (151) opposite to the discharging screw driving unit intrudes into the operational space of the receiving tray (10), characterized by that the crushing screws (11) are screws of the same pitch direction and without central shaft, provided with short drive shafts (112) on their driven end, wherein the rotational axis of the discharging screw (151) and the plane determined by the rotational axes of the two crushing screws (11) define an acute angle.

2. The crushing and sorting apparatus of claim 1, characterized by that a plurality of briar teeth (106) are arranged on the end plate (105) of the receiving tray (10) and a plurality of bits (111) are arranged on the end of the crushing screw (11).

3. The crushing and sorting apparatus of claim 2, characterized by that the pitches of crushing screws (11) are identical with each other.

4. The crushing and sorting apparatus of claim 1, characterized by that the crushing screws (11) are made of multi-layer metal sheets.

5. The crushing and sorting apparatus of claim 1, characterized by that the non-driven end of the crushing screws (11) is arranged close to the end wall.

6. The crushing and sorting apparatus of claim 1, characterized by that the crushing screws (11) are adapted to rotate independently of each other and their rotational speed is adjustable.

7. The crushing and sorting apparatus of claim 1, characterized by that the discharging screw (151) is adapted for turning back-and-forth.

8. The crushing and sorting apparatus of claim 1, characterized by that there are one or more separate discharge hoppers (153, 154) on the discharging assembly (15).

* * * * *